United States Patent
Egger et al.

(10) Patent No.: US 6,281,021 B1
(45) Date of Patent: Aug. 28, 2001

(54) USE OF DERIVATIZED REAGENTS IN CHEMILUMINESCENCE AND ELECTROCHEMILUMINESCENCE DETECTION METHODS

(75) Inventors: Martin Egger, Bernried; Hans-Peter Josel, Weilheim; Gabriele Punzmann, München, all of (DE)

(73) Assignee: Roche Diagnostics GmbH (DE)

( * ) Notice: Subject to any disclaimer, the term of this patent is extended or adjusted under 35 U.S.C. 154(b) by 0 days.

(21) Appl. No.: 09/336,085

(22) Filed: Jun. 18, 1999

(30) Foreign Application Priority Data

Jun. 25, 1998 (DE) .............................. 198 28 441

(51) Int. Cl.⁷ ..................... G01N 33/532; G01N 33/536; G01N 33/546; G01N 33/553; C07K 17/08
(52) U.S. Cl. ................. 436/544; 436/526; 436/534; 436/536; 436/825; 530/391.3
(58) Field of Search ................... 436/544, 825, 436/536, 534, 526; 530/391.3

(56) References Cited

U.S. PATENT DOCUMENTS 5,310,687   5/1994   Bard et al. .................... 436/518

FOREIGN PATENT DOCUMENTS

| 0 178 450 A2 | 4/1986 | (EP) | G01N/33/533 |
| 0 580 979 A2 | 2/1994 | (EP) | G01N/33/52 |
| WO 87/06706 | 11/1987 | (WO) | G01N/33/532 |
| WO 90/05296 | 5/1990 | (WO) | G01N/21/66 |
| WO 96/03409 | 2/1996 | (WO) | C07F/15/00 |
| WO 96/03410 | 2/1996 | (WO) | C07F/15/00 |
| WO 96/35812 | 11/1996 | (WO) | C12Q/1/68 |

*Primary Examiner*—Mary E. Ceperley
(74) *Attorney, Agent, or Firm*—Marilyn L. Amick; Roche Diagnostics Corporation

(57) ABSTRACT

The invention concerns methods for the detection of an analyte in a sample by chemiluminescence or electrochemiluminescence using derivatized test reagents. In addition new reagents and reagent kits for chemiluminescence and electrochemiluminescence detection methods are disclosed.

20 Claims, 3 Drawing Sheets

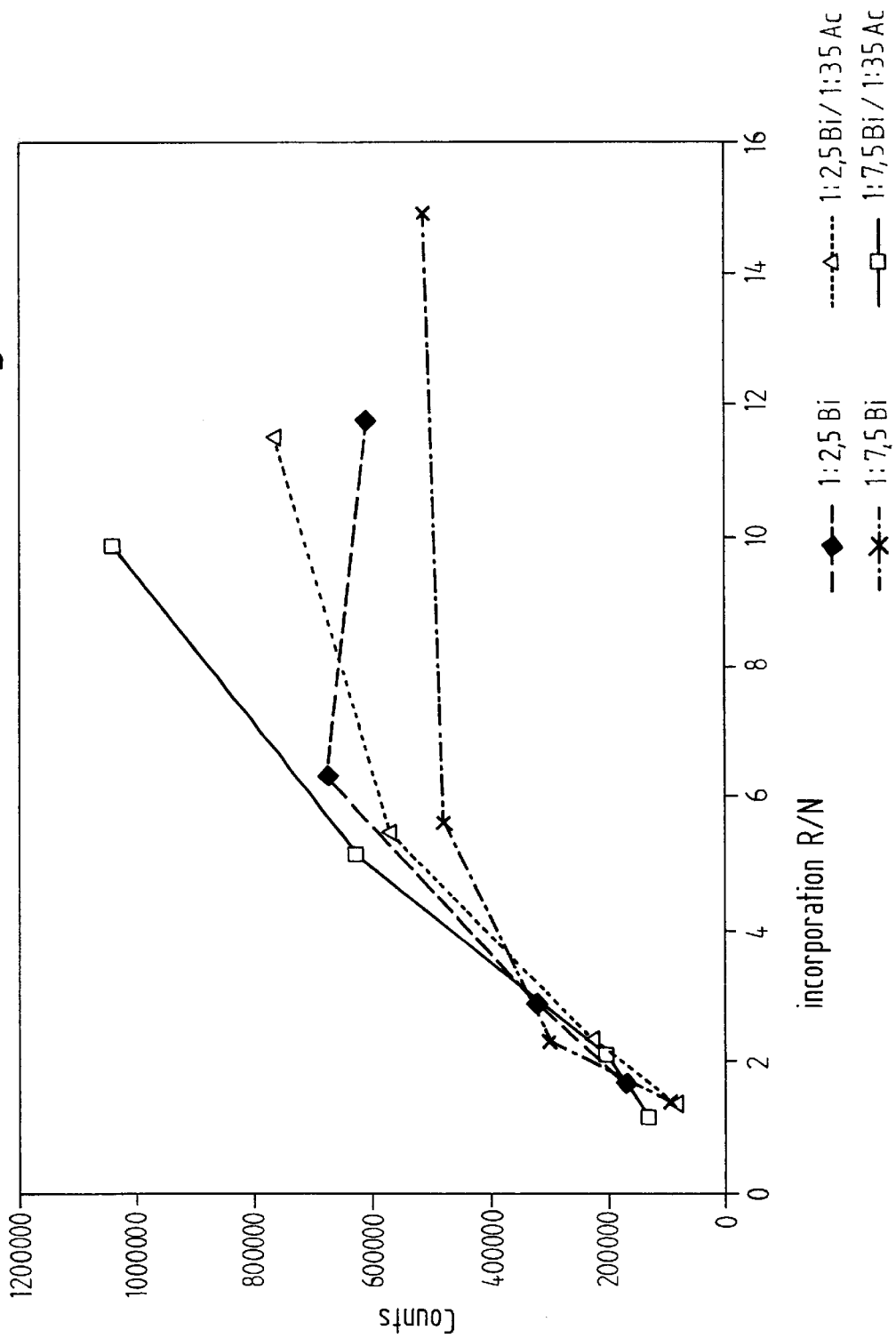

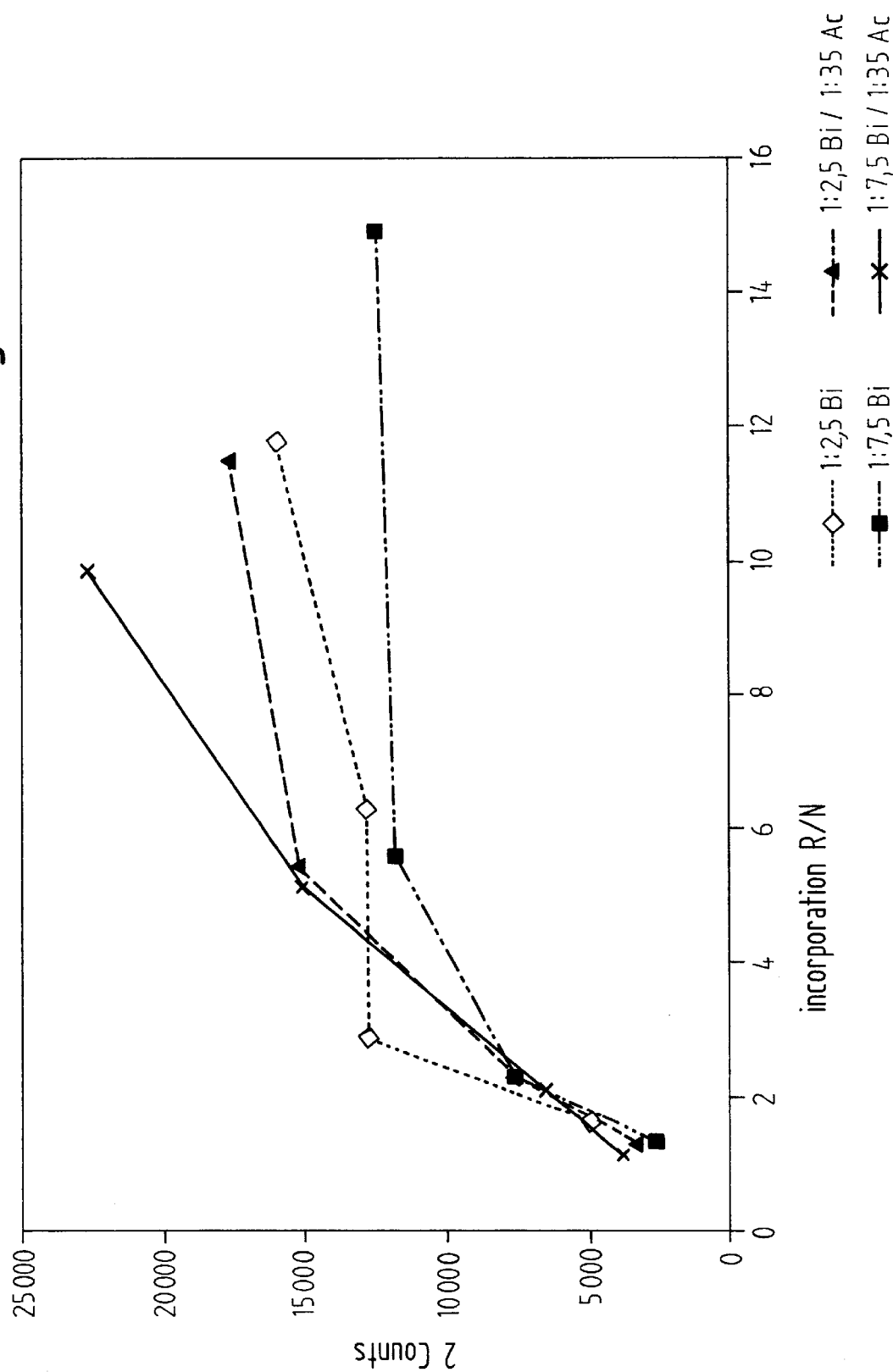

USE OF DERIVATIZED REAGENTS IN CHEMILUMINESCENCE AND ELECTROCHEMILUMINESCENCE DETECTION METHODS

The invention concerns methods for the detection of an analyte in a sample by chemiluminescence or electrochemiluminescence using derivatized test reagents. In addition new reagents and reagent kits for chemiluminescence and electrochemiluminescence detection methods are disclosed.

The detection of analytes by chemiluminescence and electrochemiluminescence is known. Thus EP-A-0 178 450 discloses conjugates of ruthenium complexes and immunologically active materials which are used as reagents in chemiluminescence detection methods. The ruthenium complexes contain three identical or different bicyclic or polycyclic ligands with at least two heterocycles containing nitrogen and at least one of these ligands is substituted by a group such as —$SO_3H$ or —COOH which renders it water-soluble and at least one of these ligands is directly substituted or substituted via a spacer group with at least one reactive group such as —COOH and the ligands are bound to the ruthenium via nitrogen atoms.

Furthermore the use of metal complexes as labelling reagents for an electrochemiluminescence detection method is known (cf. e.g. EP-A-0 580 979, WO 87/06706, U.S. Pat. No. 5,238,108 or U.S. Pat. No. 5,310,687). Such a chemiluminescence or electrochemiluminescence detection method is based on the conversion of the central atom of the metal complex e.g. ruthenium into the excited MLCT triplet state by chemical or electrochemical means in a suitable measuring device by means of an energy consuming process e.g. electron transfer from a cosubstrate such as a tripropylamine radical. From this excited state it can relax via a forbidden triplet-singlet transition into the ground state with emission of a photon (cf. e.g. WO 90/05296; Leland and Powell, J. Electrochem. Soc. 137 (1990), 3127–3131; Blackburn et al., Clin. Chem. 37 (1991), 1534–1539). However, this reaction mechanism is susceptible to numerous interferences depending on the conditions before and during the measuring phase. Thus secondary reactions can reduce the light yield even to the extent of complete quenching.

It was surprisingly discovered within the framework of the present invention that readily oxidizable chemical groups in components of the test reagent such as free amino groups can interfere with the luminescence reaction. Experiments carried out by the inventors showed that the interfering groups can be present on the molecule carrying the chemiluminescent labelling group or on separate molecules.

The inventors recognized that these oxidizable groups which interfere with the chemiluminescence detection reaction can be blocked (capped) by chemical derivatization and made inaccessible for a chemical or electrochemical reaction without concurrent unacceptable losses of sensitivity in a detection method. In particular the experimental finding is surprising and new that derivatized compounds and in particular those which carry a large number of chemiluminescent labelling groups emit more light than corresponding underivatized compounds and that in an electrochemiluminescence detection method the catalytic anodic current component of derivatized compounds which leads to an undesired reduction in the measured signal is smaller in the case of derivatized compounds than with underivatized compounds. Hence significant advantages can be achieved by using derivatized test reagents in chemiluminescence and electrochemiluminescence detection methods.

Hence a subject matter of the invention is a method for the detection of an analyte in a sample by chemiluminescence or electrochemiluminescence in which the sample is contacted with a test reagent which contains a chemiluminescent or electrochemiluminescent marker group coupled to an analyte-specific receptor and other test components and in which the method is characterized in that oxidizable chemical groups on the labelled receptor or/and on other test components are at least partially protected by derivatization.

The method according to the invention can be a chemiluminescence method i.e. a signal originating from a labelling group is generated by chemical agents. However, the method is preferably an electrochemi-luminescence method in which the light signal originating from the marker group is generated by electrochemical means. An electrochemiluminescence detection method can be carried out in known measuring devices such as a measuring chamber for holding a measuring electrode, means for feeding in and discharging liquids from the measuring chamber and means for detecting the electrochemi-luminescence generated from the measuring chamber. In addition the device can preferably have magnetic means for immobilizing magnetic particles in the sample liquid on the measuring electrode. Such measuring devices are for example described by N. R. Hoyle: "The Application of Electrochemiluminescence to Immunoassay-based Analyte Measurement", in Bioluminescence and Chemiluminescence; Proceedings of the 8th International Symposium on Bioluminescence and Chemiluminescence, Cambridge, Sep. 1994, A.K. Campbell et al., (publisher), John Wiley & Sons as well as in WO 89/10551 or W090/11511.

The method according to the invention comprises the use of test reagents in which oxidizable chemical groups which interfere with the chemiluminescence or electrochemiluminescence detection reaction are at least partially protected by derivatization i.e. no or significantly fewer oxidizable groups are converted under the test conditions. The oxidizable chemical groups are for example selected from primary amino groups, secondary amino groups, Schiff bases, thiol groups, acetal groups and ketal groups. Primary or/and secondary aliphatic or aromatic, in particular aliphatic amino groups are particularly preferred.

The oxidizable groups can be derivatized by any known methods. A particularly preferred method for derivatization is acylation especially in the case of primary or secondary amino groups. Other methods of derivatization comprise for example imide formation e.g. the introduction of a phthalimide group (starting from phthalic acid anhydride or O-methoxycarbonylbenzoyl chloride or N-ethoxycarbonylphthalimide), carbamate formation (carbamoylation) and in particular sulfonylation (e.g. the introduction of benzene-sulfonamide or p-toluenesulfonamide groups). In addition the formation of quarternary ammonium salts is also possible.

Known acylation reagents such as carboxylic acid chlorides, anhydrides or active esters can be used for the acylation. Anhydrides or/and active esters are preferred. Active esters such as N-hydroxysuccinimide esters and above all soluble derivatives thereof e.g. sulfonic acid residues are particularly preferred. Furthermore acetic acid p-nitrobenzyl esters also come into consideration. The acyl groups used for the derivatization can be preferably short-chain acyl groups such as acetyl or/and propionyl residues. On the other hand the use of hydrophilic groups e.g. acyl residues carrying hydroxyl, ether or carboxylic acid groups such as tartryl or succinyl residues or polyethyleneglycol-modified acyl residues, is also preferred.

The derivatized substances according to the invention are usually biological substances such as those that are used as test components in detection methods to determine analytes. The derivatized substances can for example be selected from cells, viruses, subcellular particles, proteins, lipoproteins, glycoproteins, peptides, polypeptides, nucleic acids, nucleic acid analogues, oligosaccharides, polysaccharides, lipopolysaccharides, cellular metabolites, haptens, hormones, pharmacological active substances, alkaloids, steroids, vitamins and amino acids. The derivatized substances are preferably selected from peptides, polypeptides, nucleic acids, nucleic acid analogues such as peptidic nucleic acids (PNA), sugars and haptens i.e. organic molecules with a molecular weight of 150 to 2000. The derivatized substances are particularly preferably selected from polypeptides such as antibodies or antibody fragments.

Metal complexes having a structure of the general formula (I) are preferably used as chemiluminescent or electrochemiluminescent labelling groups:

$$M_n(L_1L_2L_3)_m \quad (I)$$

in which

M is a divalent or trivalent metal cation selected from rare earth and transition metal cations such as ruthenium, osmium, rhenium, iridium, rhodium, platinum, indium, palladium, molybdenum, technetium, copper, chromium, tungsten, yttrium or lutetium, $L_1$, $L_2$ and $L_3$ are the same or different and are ligands with at least 2 heterocycles containing nitrogen e.g. aromatic heterocycles such as bipyridyl, bipyrazyl, terpyridyl or phenanthronyl and n and m are each independently of one another integers of 1 to 10, preferably of 1 to 3.

Ruthenium, iridium, rhenium, chromium and osmium are particularly preferred metal cations. Ruthenium is most preferred. The metal complex can also optionally contain counterions e.g. anions for charge equalization. In addition it is preferred that n and m are each 1. The complex ligands are particularly preferably selected from bipyridine and phenanthroline ring systems.

Particularly good results, especially in the case of electrochemiluminescence methods, are obtained with metal complexes which have at least one hydrophilic group or/and a charge carrier (that is different from the metal cation) in the complex. Examples of such charge carriers are phosphate, phosphonate, sulfonate and carboxylate groups, sulfonate and carboxylate groups being especially preferred. Examples of suitable hydrophilic groups are $C_2-C_3$-alkylenoxy units, $C_2-C_3$-alkylenethio units and polyhydroxy units. Such hydrophilic or/and charged metal complexes are disclosed in EP-A-0 178 540, WO 96/03409 and WO 96/03410.

Such metal complexes can be prepared according to known methods for example by reacting a metal salt, e.g. a metal halogenide, and optionally subsequently replacing the halogenide ion by hexafluorophosphate, trifluoroacetate or tetrafluoroborate groups. The metal complex is subsequently coupled to the biological substance by known methods. The resulting conjugates can then be used as detection reagents.

The method according to the invention comprises the determination of an analyte in a sample. The sample is preferably a biological sample and is in a liquid form. It can be derived from human, animal or plant tissues, body fluids, prokaryotic or eukaryotic cell cultures etc. This sample is admixed with the test reagents required to determine the respective analyte, which contain a chemiluminescent or electrochemiluminescent labelling group coupled to a biological substance and other test components known to a person skilled in the art.

The method according to the invention comprises the determination of an analyte by reaction with one or several analyte-specific receptors from the test reagent. This reaction is preferably a high affinity interaction e.g. an antigen-antibody reaction, a nucleic acid hybridization reaction or/and a sugar/lectin reaction. The method according to the invention is preferably an immunological method or a nucleic acid hybridization method.

The detection method can be carried out as a homogeneous assay i.e. the chemiluminescence or electrochemiluminescence is measured in the liquid phase. However, it is preferable to carry out a heterogeneous test in which the chemiluminescent or electrochemiluminescent label is immobilized on a solid phase e.g. a particulate solid phase such as magnetic microbeads e.g. streptavidin-coated microbeads or colloidal particles and the presence or/and the amount of the analyte is determined by means of the label immobilized on the solid phase. If a heterogeneous test is carried out the method includes so-called capture and wash steps in which the solid phase is immobilized on the electrode and a separation of the other non-bound sample components takes place.

The invention is based on the use of one or several derivatized test components in the determination of an analyte by chemiluminescence or electrochemiluminescence. In a particularly preferred embodiment the analyte-specific receptor carrying the chemiluminescent or electrochemiluminescent labelling group is used in a derivatized form. This receptor is preferably a covalent conjugate of a biological substance and one or several marker groups. The biological substance of the conjugate is analyte-specific i.e. it can directly and specifically interact with the analyte or another analyte-specific receptor (sandwich test) or it can be an analyte analogue (competitive test). The analyte-specific receptor can carry one or several labelling groups. The analyte-specific receptor is particularly preferably used in a highly labelled form i.e. it carries at least 5, and particularly preferably at least 10 labelling groups per molecule of the biological substance.

Alternatively or in addition to derivatizing the labelled analyte-specific receptor, it is also possible to use other test components in a derivatized form. Such additional test components include non-labelled analyte-specific receptors, solid phase coatings and—if present—substances which reduce interference. Non-labelled analyte-specific receptors are for example substances which are required in a sandwich test to immobilize the analyte on a solid phase or they are free receptors which can interact directly with the analyte and on which the labelled receptor then in turn binds. In the case of solid phase coatings they can be polypeptides such as antibodies or streptavidin. If reagents are used to reduce interference such as unspecific antibodies, these can also be used in a derivatized form.

The biological substances can be derivatized statistically but also selectively. A statistical derivatization of oxidizable groups is often used successfully for macromolecules such as polypeptides e.g. antibodies. In this case the biological substance is contacted with the derivatization reagent e.g. with an acylation reagent in a suitable amount and under suitable conditions in order to achieve a desired degree of derivatization which on the one hand enables a significant improvement of the chemiluminescence or electrochemiluminescence measurement signal during the detection method but on the other hand, it does not lead to a significant impairment of the test performance of the biological substance e.g. analyte specificity, ability to reduce interference etc. Reaction conditions which lead to such a suitable degree of derivatization of the biological substance can be determined in a simple manner by a person skilled in the art.

On the other hand it is also possible to selectively derivatize the test components. In this case certain groups of the biological substance are specifically derivatized. This procedure is especially suitable for smaller biological substances such as haptens, peptides and also for nucleic acids or nucleic acid analogues. Targeted derivatization reactions can be carried out in a simple manner for example in chemical syntheses of peptides, nucleic acids or peptidic nucleic acids by using suitable protecting group strategies or by using already derivatized monomer building blocks in the desired positions.

A further subject matter of the present invention is a reagent kit for the detection of an analyte comprising:

(a) an analyte-specific receptor which carries at least one chemiluminescence or electrochemiluminescence labelling group and (b) additional test components, characterized in that oxidizable chemical groups on the labelled receptor or/and on additional test components are protected by derivatization.

The additional test components include biological substances which are preferably selected from non-labelled analyte-specific receptors, solid phase coatings or/and substances which reduce interference. One or several substances from the group comprising the analyte-specific receptor and these additional test components is present in a derivatized form. Preferably at least the labelled analyte-specific receptor is derivatized. The reagent kit according to the invention can be used in a method for the detection of an analyte and in particular in one of the previously mentioned methods.

Yet a further subject matter of the invention is a conjugate of a biological substance and at least one chemiluminescent and electrochemiluminescent labelling group which is characterized in that oxidizable chemical groups on the biological substance are protected by derivatization.

The invention is further elucidated by the following examples and figures.

BRIEF DESCRIPTION OF THE DRAWINGS

FIGS. 1 and 2 show the results of cyclovoltammetric measurements of derivatized and non-derivatized ruthenium-labelled antibodies and FIGS. 3 and 4 show the size of the electrochemiluminescence measurement signal for derivatized and non-derivatized ruthenium-labelled antibodies in a heterogeneous and a homogeneous test system.

EXAMPLES

1. Preparation of Reagents

Figure 1:
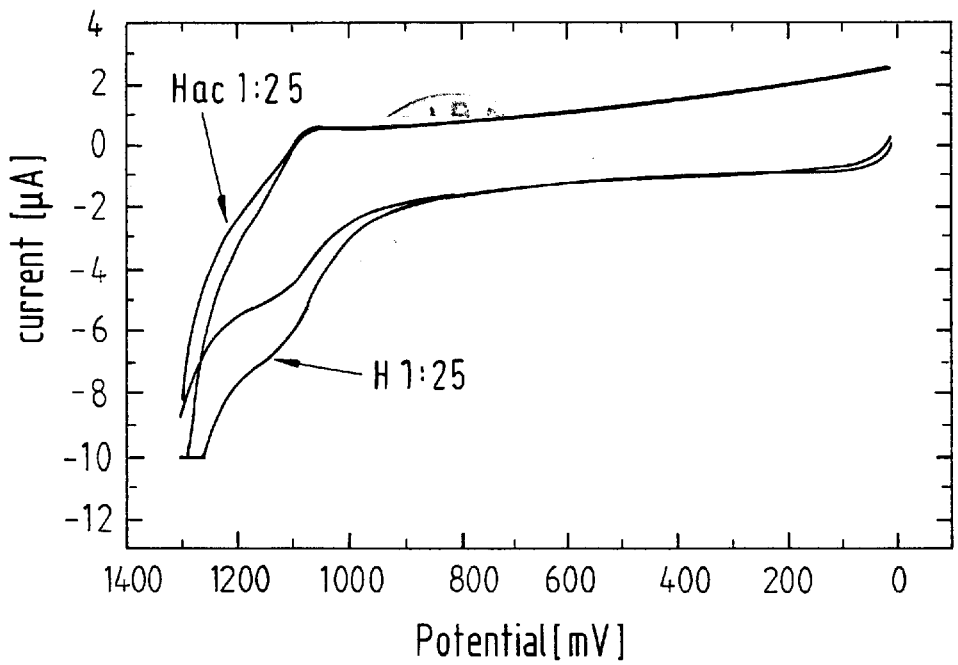

Conjugates composed of polyclonal sheep anti-T4-IgG antibodies and biotin and a ruthenium(bipyridyl)$_3$ complex (rubpy) were prepared in various degrees of biotinylation and ruthenylation.

Biotinylation:

Immunoglobulin (IgG) was dissolved in 0.1 M potassium phosphate, pH 8.4 at a concentration of 10 mg/ml. The amount of biotin-$\epsilon$-amino-caproic acid-N-hydroxy-succinimide ester required for the selected stoichiometry dissolved in 50 $\mu$l anhydrous dimethyl-sulfoxide was added per 1 ml solution. After 90 minutes stirring at 25° C., the reaction was stopped by adding 10 $\mu$mol lysine per 1 ml mixture. Then it was dialysed at 4° C. against 25 mM potassium phosphate/50 mM NaCl, pH 7.0 and the respective biotinylated IGG (IGG-BI) was lyophilized.

Ruthenylation:

The lyophilized IGG-BI (with the selected degree of biotinylation) was dissolved in 0.15 M potassium phosphate/0.15 M NaCl, pH 7.8 at a concentration of 10 mg/ml. The amount of ruthenium(2,2'-bipyridyl)$_2$(4-[3(N-hydroxysuccinimidyl-carboxy) propyl]-4'-methyl-2,2'-bipyridine required for the selected stoichiometry dissolved in 50 $\mu$l anhydrous dimethylsulfoxide was added per 1 ml solution and stirred for 90 min at 25° C.

For the conjugate variants without acetylation, the reaction was stopped immediately by adding 10 $\mu$mol lysine per 1 ml solution. In the case of the acetylated conjugate variants, 2.35 $\mu$mol acetyl-N-hydroxysuccinimide ester (dissolved in 50 ml anhydrous dimethylsulfoxide) was added per 1 ml solution (molar ratio of acetylation reagent per IGG=35:1) and stirred for a further 45 min at 25° C. Not until then was it stopped with lysine as stated above.

Both types of conjugate were dialysed against 25 mM potassium phosphate/0.15 M NaCl, pH 7.0 and then lyophilized.

Batches with a degree of biotinylation of 1:2.5 and a degree of ruthenylation of 1:2.5 (A), 1:5 (B), 1:12 (C) and 1:25 (D) and a degree of biotinylation of 1:7.5 and a degree of ruthenylation of 1:2.5 (E), 1:5 (F), 1:12 (G) and 1:25 (H) were prepared. The corresponding acetylated batches are denoted "ac".

The analytical data of these antibody batches are shown in the following table 1:

TABLE 1

| Batch No. | ml | $\epsilon$455 nm prot. | BCA | incorporation R/N | $\Sigma$ protein |
|---|---|---|---|---|---|
| Degree of biotinylation 1:2.5 | | | | | |
| A 1:2,5 | 5.3 | 1.30 | 8.9 | 1.6 | 47 mg |
| B 1:5 | 4.3 | 2.40 | 9.2 | 2.86 | 39.6 mg |
| C 1:12 | 4.5 | 5.20 | 9.06 | 6.28 | 40.8 mg |
| D 1:25 | 4.0 | 8.16 | 7.6 | 11.72 | 30.5 mg |
| Degree of biotinylation 1:7.5 | | | | | |
| E 1:2,5 | 4.5 | 1.14 | 9.48 | 1.32 | 42.7 mg |
| F 1:5 | 4.6 | 1.92 | 9.24 | 2.28 | 42.5 mg |
| G 1:12 | 4.3 | 4.86 | 9.54 | 5.58 | 41 mg |
| H 1:25 | 4.1 | 5.62 | 6.0 | 14.89 | 24.6 mg |
| Degree of biotinylation 1:2.5; degree of acetylation 1:35 | | | | | |
| Aac 1:2,5 | 3.9 | 1.06 | 8.88 | 1.31 | 34.6 mg |
| Bac 1:5 | 4.1 | 1.97 | 9.3 | 2.32 | 38.1 mg |
| Cac 1:12 | 2.27 | 4.56 | 9.18 | 5.44 | 20.8 mg |
| Dac 1:25 | 3.9 | 7.86 | 7.5 | 11.47 | 29.3 mg |
| Degree of biotinylation 1:7.5; degree of acetylation 1:35 | | | | | |
| Eac 1:2,5 | 4.1 | 0.96 | 9.36 | 1.12 | 38.4 mg |
| Fac 1:5 | 4.0 | 2.01 | 10.56 | 2.08 | 42.2 mg |
| Gac 1:12 | 3.7 | 5.00 | 10.68 | 5.13 | 39.5 mg |
| Hac 1:25 | 4.0 | 5.88 | 6.54 | 9.847 | 26.2 mg |

The total amount of protein in the mixture ($\Sigma$ protein) was determined using the BCA reagent from Pierce according to the manufacturer's instructions.

R/N denotes the average number of ruthenium complexes per 1 IGG molecule.

R denotes the amount (nmol) of ruthenium complex in 1 ml solution and is calculated from the absorbance $\epsilon$455 nm) shown in the table divided by the extinction coefficient 13.7 for the complex.

N denotes the amount (nmol) rGt in 1 ml solution and is calculated from the value of BCA protein stated in the table (mg IGG protein per 1 ml solution) by dividing it by the molecular weight factor 150 for IGG.

2. Cyclovoltammetric Measurement of the Antibody Conjugates

The measurement conditions were as follows: working electrode: glass-carbon with a diameter of 3 mm; counter electrode: Pt; reference electrode: Ag/AgCl in 3 M KCl; 100 mv/s; room temperature.

5 mg of the antibody conjugate was dissolved in 1 ml phosphate buffer (0.1 M $KH_2PO_4$+0.1 M KOH, pH 7).

Figure 2:
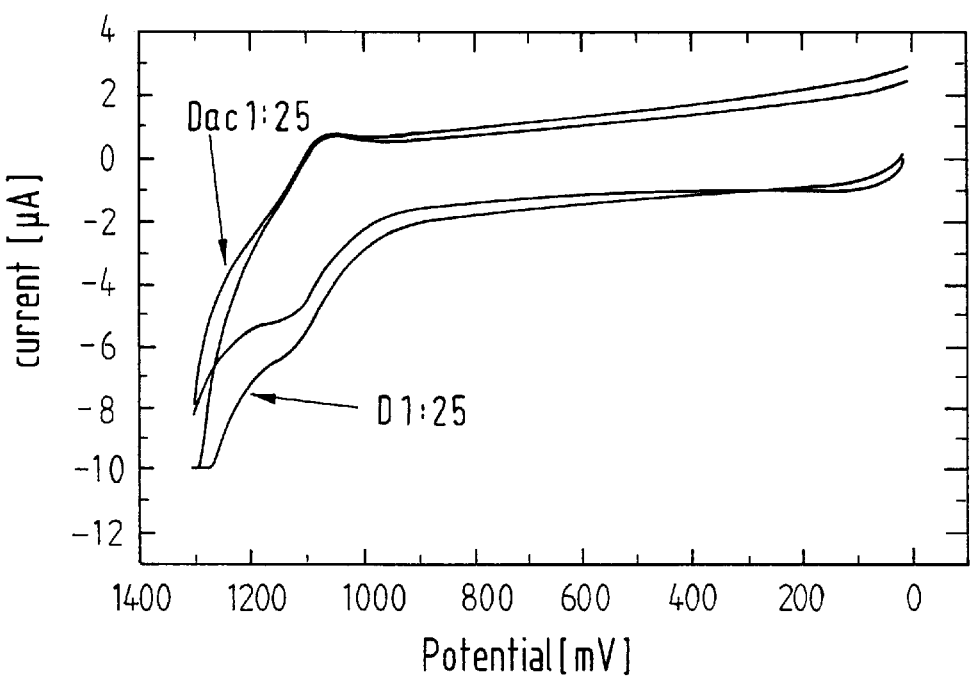

A comparison between the acetylated conjugates (Hac and Dac) and the corresponding non-acetylated conjugates (H and D) is shown in FIG. 1 and 2. These show that the oxidation current decreases after acetylation i.e. the catalytic effect of the oxidizable groups e.g. the free amino groups is suppressed by the acetylation. The reduction peak is somewhat more pronounced in FIG. 2.

It can be seen from this data that in an electrochemiluminescence detection method free amino groups in biological substances are partially oxidized by the metal cation e.g. ruthenium (III) and that this behaviour can be abolished by a derivatization by means of acetylation.

3. Influence of Acetylation on the Measured Signal

The investigation was carried out using the conjugates prepared in example 1 in a homogeneous test and in a heterogeneous test (presence of streptavidin-coated microbeads) on an Elecsys® 2010 standard instrument. Test procedure:

The conjugates in table 1 were dissolved at a concentration of 125 ng/ml in Elecsys® ProCell (0.3 M phosphate buffer+0.18 M tripropylamine+0.1% detergent, pH 6.8).

These solutions were used undiluted and measured in the homogeneous test.

In the heterogeneous test 15 $\mu$l of the conjugate solutions were incubated for 9 min at 37° C. with 185 $\mu$l of a bead suspension of 136 $\mu$g streptavidin-coated beads/ml. The beads were measured after a bound-free separation.

Both applications were carried out on an Elecsys® 2010 instrument.

As a result of these investigations it was found that, especially in the case of highly biotinylated conjugates (E to H), a significant increase of the measured signal is found due to the acetylation. In the case of the less biotinylated conjugates (A to D) this effect is less pronounced.

In addition it was found that a non-acetylated conjugate does not yield a higher measurement signal beyond a degree of ruthenylation >1:12 in the homogeneous as well as in the heterogeneous test. A significant increase in the measurement signal was achieved by capping.

The result of these investigations is summarized in FIG. 3 (heterogeneous test) and 4 (homogeneous test).

What is claimed is:

1. A method for the detection of an analyte in a sample by chemiluminescence or electrochemiluminescence in which the sample is contacted with a test reagent comprising at least one chemiluminescent or electrochemiluminescent labelling group coupled to an analyte-specific receptor and other test components, wherein the labelling group is selected from the group consisting of metal complexes having a structure of the general formula $M_n(L_1L_2L_3)_m$ in which M is a divalent or trivalent metal cation selected from rare earth and transition metal cations, $L_1$, $L_2$ and $L_3$ are the same or different and are ligands with at least 2 heterocycles containing nitrogen, and n and m are each independently of one another integers of 1 to 10, wherein the oxidizable chemical groups on the labelled receptor and optionally on other test components are protected by derivatization, and a signal from the labelling group is detected as a measure of the analyte in the sample.

2. The method of claim 1 wherein the oxidizable chemical groups are selected from the group consisting of primary amino groups, secondary amino groups, Schiff's bases, thiol groups, acetal groups and ketal groups.

3. The method of claim 2 wherein the oxidizable chemical groups are selected from the group consisting of primary and secondary amino groups.

4. The method of claim 1 wherein the derivatization is carried out by an acylation.

5. The method of claim 4 wherein the acylation is carried out by using an anhydride or an active ester or both.

6. The method of claim 5 wherein the active ester is selected from N-hydroxysuccinimide esters, derivatives thereof and acetic acid-p-nitrobenzyl ester.

7. The method of claim 4 wherein the acylation is carried out with at least one of an acetyl residue and a propionyl residue.

8. The method of claim 4 wherein the acylation is carried out with acyl residues carrying hydrophilic groups or polyethylene glycol-modified acyl residues.

9. The method of claim 1 wherein the receptor is selected from peptides, polypeptides, nucleic acids, nucleic acid analogs, sugars and haptens.

10. The method of claim 9 wherein the receptor is selected from antibodies and antibody fragments.

11. The method of claim 1 wherein the metal cation is ruthenium.

12. The method of claim 1 wherein it is carried out as a heterogeneous test in which the label is immobilized on a solid phase and the presence and/or the amount of the analyte is determined by means of the label immobilized on the solid phase.

13. The method of claim 12 wherein a particulate coated solid phase is used.

14. The method of claim 1 wherein the labelled analyte-specific receptor carries at least 5 labelling groups.

15. The method of claim 1 wherein a non-labelled analyte-specific receptor is used in a derivatized form.

16. The method of claim 1 wherein a solid phase coating in a derivatized form is used.

17. The method of claim 1 wherein an interference-reducing reagent is used in a derivatized form.

18. A reagent kit for the detection of an analyte, the kit comprising:
(a) an analyte-specific receptor which carries at least one chemiluminescence or electrochemiluminescence labelling group, wherein the labelling group is selected from the group consisting, of metal complexes having a structure of the cyeneral formula $M_n(L_1L_2L_3)_m$ in which M is a divalent or trivalent metal cation selected from rare earth and transition metal cations, $L_1$, $L_2$ and $L_3$ are the same or different and are ligands with at least 2 heterocycles containing nitrogen, and n and m are each independently of one another integers of 1 to 10 and
(b) additional test components, wherein oxidizable chemical groups on the labelled receptor and optionally on additional test components are protected by derivatization.

19. The kit of claim 18 wherein the additional test components are selected from the group consisting of non-labelled analyte-specific receptors, solid phase coatings and substances that reduce interference.

20. A conjugate of a biological substance and at least one chemiluminescent or electrochemiluminescent labelling group, wherein the labelling group is selected from the group consisting of metal complexes having a structure of the general formula $M_n(L_1L_2L_3)_m$ in which M is a divalent or trivalent metal cation selected from rare earth and transition metal cations, $L_1$, $L_2$ and $L_3$ are the same or different and are ligands with at least 2 heterocycles containing nitrogen, and n and m are each independently of one another integers of 1 to 10, wherein the oxidizable chemical groups on the biological substance are protected by derivatization.

* * * * *